United States Patent
Yokosawa et al.

(10) Patent No.: US 8,614,574 B2
(45) Date of Patent: Dec. 24, 2013

(54) NUCLEAR MAGNETIC RESONANCE IMAGING APPARATUS

(75) Inventors: Suguru Yokosawa, Kokubunji (JP); Yo Taniguchi, Kokubunji (JP); Yoshitaka Bito, Kokubunji (JP); Hiroyuki Itagaki, Fuchu (JP)

(73) Assignee: Hitachi Medical Corporation, Tokyo (JP)

(*) Notice: Subject to any disclaimer, the term of this patent is extended or adjusted under 35 U.S.C. 154(b) by 476 days.

(21) Appl. No.: 12/993,905

(22) PCT Filed: May 22, 2009

(86) PCT No.: PCT/JP2009/059444
§ 371 (c)(1),
(2), (4) Date: Nov. 22, 2010

(87) PCT Pub. No.: WO2009/142300
PCT Pub. Date: Nov. 26, 2009

(65) Prior Publication Data
US 2011/0133735 A1    Jun. 9, 2011

(30) Foreign Application Priority Data

May 22, 2008    (JP) .................................. 2008-134644

(51) Int. Cl.
*G01V 3/00* (2006.01)
*A61B 5/05* (2006.01)
*G01R 33/48* (2006.01)

(52) U.S. Cl.
USPC ........... 324/307; 324/309; 324/318; 324/322; 600/410

(58) Field of Classification Search
USPC ............................ 324/300–322; 600/407–464
See application file for complete search history.

(56) References Cited

U.S. PATENT DOCUMENTS 4,808,928 A * 2/1989 Frahm et al. ............ 324/309
7,868,618 B2 * 1/2011 Taniguchi et al. ........ 324/318
(Continued)

FOREIGN PATENT DOCUMENTS

| JP | 9-262220    | 10/1997 |
| JP | 2004-209084 | 7/2004  |
| JP | 2005-524453 | 8/2005  |

OTHER PUBLICATIONS

JP Office Action for Japanese Application No. 2008-134644, issued on Dec. 11, 2012.
(Continued)

*Primary Examiner* — Melissa Koval
*Assistant Examiner* — Emily Chan
(74) *Attorney, Agent, or Firm* — Antonelli, Terry, Stout & Kraus, LLP.

(57) ABSTRACT

A magnetic resonance imaging apparatus is provided, which is capable of reducing SAR while maintaining S/N ratio and image contrast in a GrE-type pulse sequence, regardless of whether a synchronous imaging is performed or not.

The present invention controls a flip angle as to each measurement set 409 that is obtained by division according to the size of phase encoding and a body motion cycle of a subject in the GrE-type pulse sequence. In a set 501 which measures echoes with phase encoding having a minimum absolute value, the flip angle is maximized as to the RF pulse having a minimum phase encoding amount and at least one RF pulse irradiated immediately before. As for the other RF pulses, the flip angle varies within a range less than the maximum, irrespective of the non-imaging mode, the imaging mode, or the size of phase encoding.

16 Claims, 13 Drawing Sheets

(56) References Cited

U.S. PATENT DOCUMENTS

| 8,115,486 | B2* | 2/2012 | Habara et al. | 324/318 |
|---|---|---|---|---|
| 2004/0133096 | A1* | 7/2004 | Taniguchi et al. | 600/410 |
| 2005/0240095 | A1* | 10/2005 | Schaffter | 600/410 |
| 2008/0319301 | A1* | 12/2008 | Busse | 600/410 |

OTHER PUBLICATIONS

Deshpande et al., "Improved Cardiac Cine Imaging at 3T Using Modulated Flip Angles," Proc. Intl. Soc. Mag. Reson. Med 11, 2004, p. 1813.

Jung et al.,"SSRP Cardiac Cine Imaging With High Blood—Myocardium Contrast at 3T," Proc. Intl. Soc. Mag. Reson. Med. 11, 2004, p. 1809.

Lin et al.,"Improvements of 3DTOF MRA at 3.0T," Proc. Intl. Soc. Mag. Reson. Med. 11, 2004, p. 2573.

Paul et al.,"SAR-Reduced Truefisp Using Variable Flip Angls: Influence on In-Plane Resolution and SNR Properties," Proc. Intl. Soc. Mag. Reson. Med. 15, 2007, p. 1650.

Paul et al.,"Steady State Free Precessing Imaging With High Flip Angles at 3T," Proc. Intl. Soc. Mag. Reson. Med. 11, 2004, p. 2662.

Paul et al.,"T2-Weighted B-SSFP Imaging Using Tide," Proc. Intl. Soc. Mag. Reson. Med. 13, 2005, p. 98.

* cited by examiner (i) 501

(ii) 502

NUCLEAR MAGNETIC RESONANCE IMAGING APPARATUS

TECHNICAL FIELD

The present invention relates to a nuclear magnetic resonance imaging technique that is capable of reducing a specific absorption rate (SAR).

BACKGROUND ART

A magnetic resonance imaging (MRI) apparatus is a diagnostic imaging apparatus for medical use, primarily utilizing nuclear magnetic resonance phenomena of proton. This apparatus applies a radio frequency pulse to a subject placed in a static magnetic field, exciting nuclear magnetization, and measures a magnetic resonance signal. On this occasion, application of a gradient magnetic field provides positional information, and creates a image. The MRI apparatus sets up no limitations on a portion to be imaged, allowing any cross section to be imaged noninvasively.

In general, while applying a slice gradient magnetic field which specifies a plane on which a tomographic image of the subject is to be obtained, the MRI apparatus simultaneously provides an excitation pulse in order to excite magnetizations in the plane. Accordingly, nuclear magnetic resonance signals (echoes) are obtained, which are generated in the course of precession of the magnetization excited by the pulses. In order to provide the magnetization with positional information, the MRI apparatus applies a phase-encoding gradient magnetic field and a readout gradient magnetic field, which are perpendicular with each other within the tomographic plane, during the time from the excitation to the echo acquisition. Then, the echoes being measured are arranged in a k-space which defines its horizontal axis as "kx" and the vertical axis as "ky". One echo occupies one line which is parallel to the kx-axis. The k-space is inverse Fourier transformed to reconstruct an image.

The pulse and each of the gradient magnetic fields for producing the echo are applied according to a predetermined pulse sequence. There are known different types of pulse sequences for different purposes. By way of example, a gradient echo (GrE) type high-speed imaging method is a method which repeatedly executes its pulse sequence, and allows the phase-encoding gradient magnetic field to vary sequentially for every repetition to sequentially measure the echoes in a number required for obtaining one tomographic image.

One example of this GrE-type pulse sequence is a phase compensation type pulse sequence. In this pulse sequence, a gradient magnetic field pulse is added to GrE so as to bring zero to a time integration value of the gradient magnetic field of each axis. A degree of a flip angle of the radio frequency (RF) magnetic field pulse is generally larger than that used in the other GrE type pulse sequences, and the phase thereof is inverted alternately. In addition, the repetition time (TR) is shorter and it is around 5 ms.

The GrE type imaging method as described above repeatedly excites magnetization, before executing a pulse sequence for measuring echoes required for reconstructing an image (imaging mode), in order to obtain a steady state of magnetization. This is referred to as anon-imaging mode. In the non-imaging mode, the same pulse sequence as that used in the imaging mode is executed for a given number of times without measuring echoes. In many cases, however, in order to shift the magnetization to the steady state with less times of execution, the flip angle of the RF pulse in the non-imaging mode may be gradually increased from a small angle and made closer to the angle used in the imaging mode.

Moreover, in the high-speed imaging methods as described above, the flip angle greatly influences imaging contrast. Therefore, an angle providing a particular image contrast is chosen typically from the range of 1 to 90 degrees as the flip angle for the imaging mode, and the flip angle is not usually changed during the imaging mode.

Such GrE-type high speed imaging methods as described above are frequently used for clinically conducting cardiac diagnosis, vascular diagnosis on the thoracicoabdominal part, or the like. In the case of taking an image of the heart, there is widely employed a method which enhances time resolution of the imaging by using the ECG (electrocardiogram) gating, since the cardiac cycle is short, i.e., approximately one second. In other words, this method changes the phase encoding in sync with triggering of R wave in an electrocardiogram, and measures echoes required for reconstructing one image across multiple heart beats. Breathing during the imaging causes a body motion, and this may generate a ghost in the reconstructed image. Therefore, it is general to conduct the imaging during breath-hold. When taking an image of the heart, the information as to the movement during the cardiac cycle is important, and therefore moving images (cine images) are frequently taken.

A part targeted for imaging, such as the thoracicoabdominal part which is influenced by body motion caused by breathing, is typically subjected to the imaging with breath-hold. If it is not possible to take all the images while holding the breath, measurement of echoes the number of which is necessary for reconstructing an image is divided into multiple imaging times, and the images are taken by repeating the breath-hold and the measurement. However, such imaging that repeats the breath-hold as described above may place burden on a patient, and therefore, there is a respiratory gated method which takes an image while monitoring the state of breathing under the condition of free breathing. As a method for monitoring the respiration, following methods may be employed; a method using an external device for directly measuring the respiration state, a method for incorporating another imaging for measuring the respiration state into the image taking (e.g., see the patent document 1).

On the other hand, in MRI, a magnetic resonance frequency becomes higher in proportion to the magnetic field intensity. In this connection, there arises a problem of increase in absorption of RF electric power into human bodies, called specific absorption rate (SAR), and development of countermeasure against this problem constitutes a subject of researches. The SAR indicates RF irradiation power per unit time, and it is proportional to the time integration value of square of the flip angle. A reference value of the maximum SAR for total human body is defined to be 4 W/kg. When a GrE type pulse sequence is used, the RF irradiation is repeated in a short period time, and therefore the SAR becomes large. In particular, phase compensation type GrE pulse sequences use a short TR and a large flip angle. Therefore, it is difficult to apply such sequence to a human body in a high magnetic field apparatus using a magnetic field of about 3 Tesla or more in view of safety. By way of example, for the case that a phase compensation type GrE pulse sequence using the flip angle of 60 degrees and TR of 3 ms is executed in an apparatus using the magnetic field of 3 Tesla, the SAR is calculated to be 4.7 W/kg. This value exceeds the reference value, and therefore it is impossible to perform imaging.

In order to reduce SAR, it is necessary to prolong the repetition time TR or to make the flip angle smaller. However, it is not preferable to extend TR since this may cause extension of the imaging time. On the other hand, if the flip angle is made smaller, it may degrade contrast and an S/N ratio.

To solve this problem, in consideration of the specific absorption rate SAR, there has been proposed a method of changing the flip angle of RF excitation pulse for the imaging mode according to the amount of phase encoding so that the S/N ratio should not be lowered (Patent document 2). This method is based on the fact that the S/N ratio in MRI is generally determined by the S/N ratio of echoes having a small phase encoding amount, and maximizes the flip angle when an absolute value of the phase encoding amount is minimum, whereas minimizes the flip angle when an absolute value of the phase encoding amount is maximum, so that the S/N ratio should not be reduced even when the flip angle is changed.

PRIOR ART DOCUMENT

Patent Document

[Patent document 1]
JP-A-2004-209084
[Patent document 2]
JP-T-2005-524453

SUMMARY OF THE INVENTION

Problem to be Solved by the Invention

Image contrast is dependent on history of the flip angle, not only the flip angle of an RF excitation pulse irradiated when measuring an echo having a small phase encoding amount, but also the flip angles of the RF excitation pulses having been irradiated by the time of measuring the echo which has the small phase encoding amount. Therefore, according to the technique described in the patent document 2, a problem of image contrast degradation may occur, even though the S/N ratio can be maintained, when it is compared to the case where the imaging is performed keeping the flip angle constant as conventionally done.

In addition, the technique as described in the patent document 2 does not consider at all, the imaging method which divides and measures the echoes required for reconstructing an image according to ECG-gating, respiration-gating, or the like, nor the non-imaging mode for obtaining the steady state of magnetization. In the case of synchronous imaging, the number of times for performing the non-imaging mode is increased. Therefore, it is not possible to sufficiently reduce SAR by controlling the flip angle only in the imaging mode as described in the patent document 2. If multi-phase images are acquired in a particular cycle, such as the case of cine imaging, there arises a problem that contrast varies phase by phase, when the flip angle is modulated as described in the patent document 2.

The present invention has been made considering the problems above, and the object of the invention is to provide a method for reducing SAR, while maintaining the S/N ratio and the image contrast.

Means to Solve the Problem

In order to achieve the object above, the present invention provides a nuclear magnetic resonance imaging apparatus as described below. In other words, the apparatus includes, a static magnetic field application part for applying a static magnetic field to a subject, a gradient magnetic field application part for applying a gradient magnetic field to the subject, a radio frequency pulse irradiator for irradiating the subject with a radio frequency pulse, a detector for detecting a nuclear magnetic resonance signal from the subject, and a controller for controlling the radio frequency pulse irradiator, the gradient magnetic field application part, and the detector, to execute a predetermined imaging pulse sequence. The controller executes one or more sequence group, as the imaging pulse sequence, including irradiation of multiple radio frequency pulses and application of multiple gradient magnetic fields for providing multiple types of phase encoding amount, and sets a flip angle to the radio frequency pulse as to each of the one or more sequence group. By setting the flip angle with respect to each sequence group, it is possible to reduce SAR while preventing reduction of S/N ratio and degradation of image contrast.

By way of example, the sequence group has a configuration incorporating a non-imaging mode which includes irradiation of the radio frequency pulse, not accompanied by a detection of the nuclear magnetic resonance signal, and an imaging mode which includes irradiation of the radio frequency pulse, accompanied by the detection of the nuclear magnetic resonance signal.

In the case where two or more sequence groups are provided, it is preferable to configure such that the controller sets a maximum value as the flip angle to the sequence group which executes the phase encoding of an amount having a minimum absolute value, among the two or more sequence groups, and sets a value smaller than the maximum value as the flip angle to the other sequence group. With this configuration, it is possible to obtain a large signal as a nuclear magnetic resonance signal acquired by the phase encoding having a minimum absolute value, and accordingly, image quality is improved.

For example, the controller is capable of setting a substantially constant value as the flip angle to the radio frequency pulse more than one, as to each of the sequence groups.

The controller is, for instance, capable of setting a maximum flip angle to the radio frequency pulse within a repetition time for performing the phase encoding having a minimum absolute value and at least one radio frequency pulse immediately before, among the radio frequency pulses more than one included in the sequence group having the minimum absolute value of the phase encoding amount, whereas the flip angle having a value smaller than the maximum value is set to the other radio frequency pulse. Accordingly, SAR can be further reduced.

It is possible to configure the sequence group to include measurement of multiple time phases.

The controller has a configuration, for instance, which obtains by operation a specific absorption rate of the imaging pulse sequence as a whole, and determines a value of the flip angle to be set to the other sequence group so that the specific absorption rate being obtained becomes equal to or less than a predetermined safety level value.

The controller is, for instance, capable of the configuring a value of the flip angle to be set to the other sequence group, in such a manner that the flip angle of the radio frequency pulse varies sequentially, the pulse being irradiated for detecting the nuclear magnetic resonance signal, in the case where the nuclear magnetic resonance signals being measured are arranged in accordance with the size of the phase encoding.

The controller is configured, for instance, in such a manner that in the other sequence group in which the flip angle is set to be a value smaller than the maximum value, the same size flip angle is set to the radio frequency pulse to which the same size phase encoding is applied for exciting the nuclear magnetic resonance signal.

The controller is further capable of executing alternately in time series, the sequence group to which the flip angle being the maximum value is set, and the sequence group to which a value smaller than the maximum value is set.

The controller is further capable of setting the flip angle which is modulated as to each of the radio frequency pulse, in the sequence group which executes only the phase encoding of the amount having a non-minimum absolute value.

The controller may also be configured in such a manner that it changes the flip angle sequentially in units of sequence group, for two or more sequence groups which are executed in time series.

The flip angle set by the controller, being substantially constant, may be assumed as having an error within 10%.

The controller is configured, for instance, in such a manner that when the phase encoding in the sequence group including the phase encoding of the amount having a minimum absolute value is changed in time series from a negative minimum value to a positive maximum value, a maximum value is set to an associated flip angle while the phase encoding is changed from a negative minimum value to a minimum absolute value, whereas the associated flip angle is decreased gradually, while the phase encoding is changed from the minimum absolute value to the positive maximum value.

The controller is further configured in such a manner that, when the phase encoding in the sequence group including the phase encoding of the amount having a minimum absolute value is changed in time series from the minimum absolute value to a maximum absolute value, a maximum value is set to the flip angle associated with the phase encoding having the minimum absolute value, and in the subsequent stage, the flip angle is decreased gradually.

The controller is further configured in such a manner that, when the phase encoding in the sequence group including the phase encoding of the amount having a minimum absolute value is changed in time series from the maximum absolute value to the minimum absolute value, the controller gradually increases the flip angle in time series from when the phase encoding is the maximum absolute value, and sets a maximum value to the flip angle associated with the phase encoding having the minimum absolute value and to the flip angle associated with predetermined number of phase encoding before the phase encoding having the minimum absolute value.

An image reconstruction part for reconstructing an image from the nuclear magnetic resonance signal is capable of correcting intensity of the nuclear magnetic resonance signal detected by the radio frequency pulse having the flip angle smaller than the maximum value, according to the flip angle at which the irradiation is performed. The image reconstruction part is, for instance, capable of correcting the intensity of the nuclear magnetic resonance signal detected by the radio frequency pulse having the flip angle smaller than the maximum value, to agree with the intensity of the nuclear magnetic resonance signal detected by the radio frequency pulse having the flip angle which is the maximum value.

It is further possible to divide the sequence group into two or more, according to a cycle of body motion of the subject.

Effect of the Invention

According to the present invention, regardless of the presence or absence of gating, it is possible to reduce SAR while maintaining the contrast and the S/N ratio which are equivalent to those in the case where the flip angle is kept constant.

BEST MODE FOR CARRYING OUT THE INVENTION

Hereinafter, one embodiment of the present invention will be described with reference to the accompanying drawings.

First Embodiment

Figure 1:
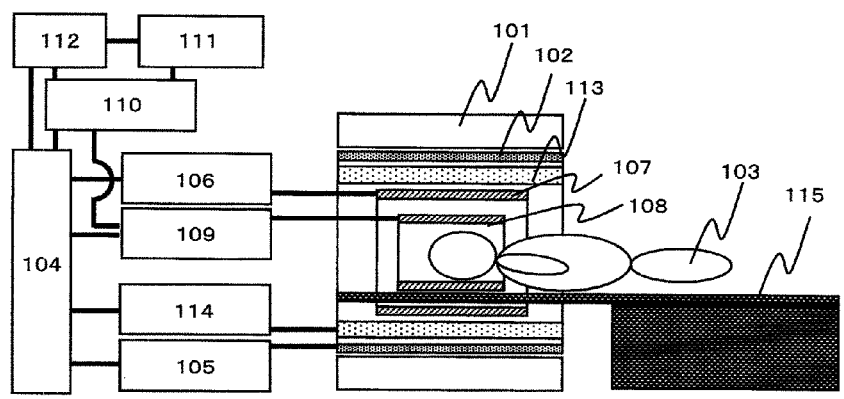
FIG. 1 is a block diagram showing an overall configuration of a nuclear magnetic resonance imaging apparatus according to the first embodiment.

Firstly, a nuclear magnetic resonance imaging apparatus according to the first embodiment will be explained. FIG. 1 illustrates a typical configuration of the nuclear magnetic resonance imaging apparatus to which the present invention is applied. This MRI apparatus includes a magnet 101 for generating a static magnetic field; a gradient magnetic field coil 102 for generating a gradient magnetic field; an RF coil 107 for irradiating a subject (living body) 103 with a radio frequency pulse (hereinafter, referred to as "RF pulse"), and an RF probe 108 for detecting a nuclear magnetic resonance signal (echo) generated from the subject 103. The subject (e.g., living body) 103 is placed on a bed (table) 115 within space of the static magnetic field generated from the magnet 101.

The gradient magnetic field coil 102 is connected to a gradient magnetic field power supply 105. The RF coil 107 is connected to radio frequency pulse generator 106. The RF probe 108 is connected to a receiver 109. A sequencer 104 sends a command to the gradient magnetic field power supply 105 and the radio frequency pulse generator 106 to generate a gradient magnetic field and a radio frequency pulse, respectively. Then, an RF pulse is applied to the subject 103 via the RF coil 107, and simultaneously, the gradient magnetic field coil 102 applies a gradient magnetic field pulse for providing an echo signal with positional information such as slice selection and phase encoding. The RF probe 108 receives a signal generated from the subject 103, and the receiver 109 performs detection. The sequencer 104 sets nuclear magnetic resonance frequency which acts as a reference of the detection. The signal being detected is transmitted to the signal processor 110, and the signal processor performs signal processing such as image reconstruction. A result of the processing is displayed on a display 111. If required, it is possible to store signals being detected, measurement conditions, and results, on a storage medium 112.

Between the gradient magnetic field coil 102 and the RF coil 107, there are arranged shim coils 113 for adjusting homogeneity of the static magnetic field. The shim coils 113 are used as appropriate so as to achieve a predetermined homogeneity of the static magnetic field. The shim coils 113 are made up of multiple channels, and the shim power supply 114 supplies electric current to those coils. When the static magnetic field homogeneity is adjusted, the sequencer 104 controls the current which flows in each of the shim coils. The sequencer 104 sends a command to the shim power supply 114, and allows the coils 113 to generate an additional magnetic field to correct static magnetic field inhomogeneity.

The sequencer 104 is a means for controlling operations of each unit, and performs control so that each unit operates at preliminarily programmed timing and intensity. Among the programs, in particular those describing information of the timing and intensity of the radio frequency pulse, the gradient magnetic field, and signal receiving are referred to as a pulse sequence. The MRI according to the present embodiment incorporates a GrE-type pulse sequence, which executes an imaging mode for measuring echoes required for reconstructing an image, and a non-imaging mode for obtaining a steady state of nuclear magnetization prior to the imaging mode. In the non-imaging mode, the magnetization is repeatedly excited so as to obtain the steady mode of the magnetization. Specific embodiments as to the control of the flip angle for each mode will be described later.

Figure 2A:
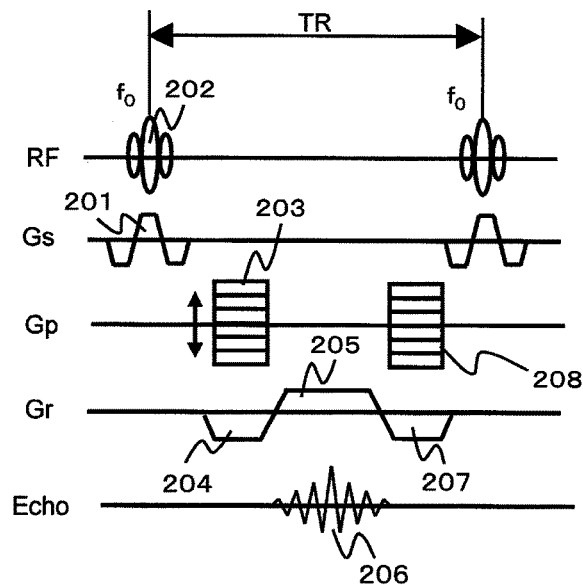
FIG. 2(a) illustrates a pulse sequence of the phase compensation type gradient echo method.

Various GrE-type pulse sequences are publicly known, and any of them may be employed depending on a portion or tissue as an imaging target. FIG. 2(a) illustrates a pulse sequence of the phase compensation type SSFP (Steady State Free Precession). Operations of this pulse sequence are described as the following. Together with applying a slice gradient magnetic field pulse 201 in the z-direction, there is applied a radio frequency pulse (RF pulse) 202 for exciting magnetization having resonance frequency f0 of proton, and then a nuclear magnetic resonance phenomenon is induced in the proton of the slice existing in the subject 103. Subsequently, a phase encoding gradient magnetic field pulse 203 for adding to the magnetization phase, positional information in the phase encoding direction (y), and a readout gradient magnetic field pulse for dephasing 204 are applied, and thereafter, a nuclear resonance signal (echo) 206 is measured while applying a readout gradient magnetic field pulse 205 for adding positional information in the readout direction (x). After measuring the echo, a phase encoding gradient magnetic field pulse for rephasing 207 and a readout gradient magnetic field pulse for rephasing 208 are applied to resume the phase of the magnetization, thereby preparing for the next excitation. As thus described, this pulse sequence applies the gradient magnetic field pulses in such a manner that a time integration value of each axis becomes zero.

Figure 2B:
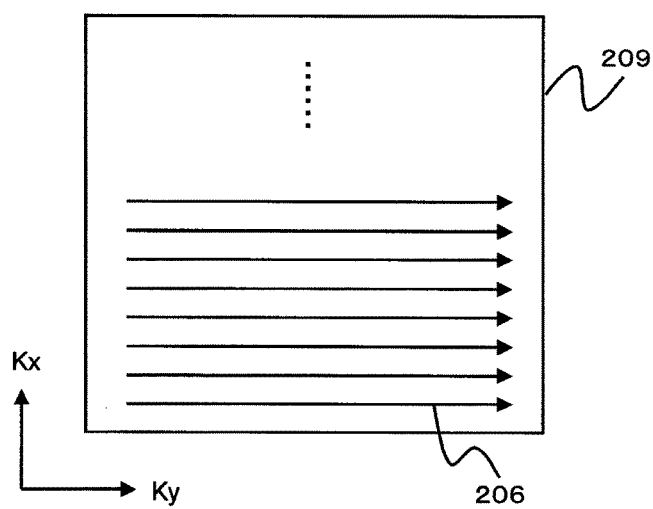
FIG. 2(b) illustrates a k-space.

The above-described procedure from the application of the slice gradient magnetic field pulse to the echo measurement is repeated by the repetition time TR, and accordingly, echoes required to obtain one image are measured. As shown in FIG. 2(b), each of the echoes are arranged on the k-space 209 which defines values of the phase encoding gradient magnetic field pulse 203 as kx-direction, and the values of the readout gradient magnetic field pulse 205 as ky-direction, and an image is reconstructed by a two-dimensional inverse Fourier transform. This pulse sequence provides the contrast reflecting T2 (transverse relaxation time)/T1 (longitudinal relaxation time), achieving favorable contrast between tissue and blood. Therefore, it is suitable for morphological and functional diagnosis of the heart, or morphological diagnosis of the abdominal part.

As for the pulse sequence described above, an explanation has been made regarding a Cartesian-type signal acquisition method. It is further possible to employ a radial scan which additionally combines biaxial read-out, or a 3 D-GrE pulse sequence which uses phase encoding also for the slice axis.

Prior to the imaging mode, the non-imaging mode is executed for obtaining the steady-state of the nuclear magnetization. In the non-imaging mode, the magnetization is repeatedly excited so that the magnetization is put into the steady state. Therefore, in the non-imaging mode, a sequence similar to the sequence of the imaging mode as shown in FIG. 2(a) is executed for a predetermined number of times. It is to be noted that in the non-imaging mode, the echo 206 is not measured. In order to shift the magnetization into the steady state by a small number of execution times, there is employed in many cases, a method that the flip angle of the RF pulse in the non-imaging mode is made to approach the angle of the imaging mode gradually starting from a small angle.

Next, an explanation will be made as to a control of the flip angle of the RF pulse 202 in the imaging mode and in non-imaging mode.

Figure 3A:
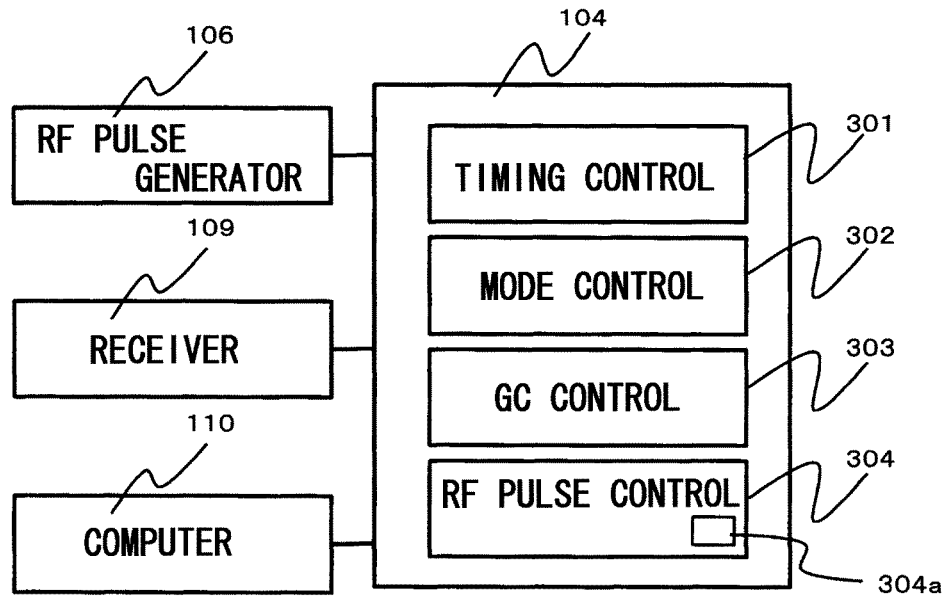
FIG. 3(a) is a block diagram showing the configuration of the sequencer in the apparatus as shown in FIG. 1.
Figure 3B:
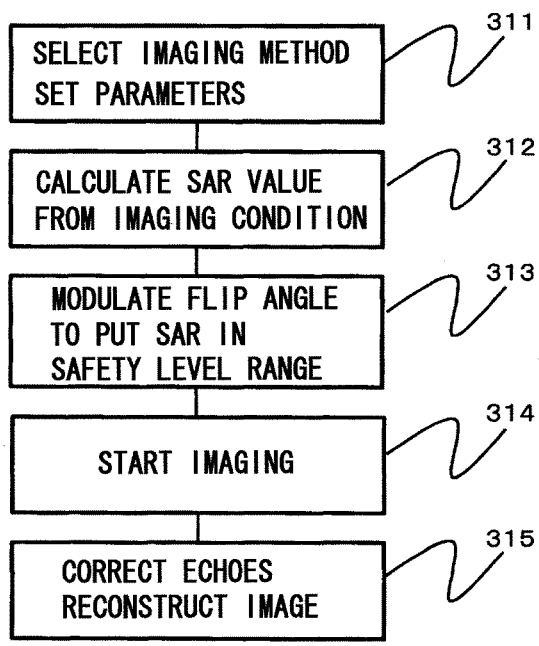
FIG. 3(b) is a flowchart showing the operation thereof.

FIG. 3(a) and FIG. 3(b) respectively illustrate a configuration and a procedure of the sequencer 104 for controlling the pulse sequence. As shown in FIG. 3(a), the sequencer 104 is made up of a timing controller 301 for controlling the application of each of the magnetic field pulses in the aforementioned pulse sequence and the timing of measuring the echo, a mode controller 302 for switching between the non-imaging mode and the imaging mode, a GC controller 303 for controlling intensity of the gradient magnetic field pulse, an RF pulse controller 304 for controlling a frequency and intensity of the RF pulse, and others. The RF pulse controller 304 is provided with a flip angle controller 304a, and others. These units in this configuration are implemented when a CPU executes programs stored in advance in a memory that is built in the sequencer 104. An operator is allowed to set required conditions and parameters via an input means provided in the signal processor 110.

As shown in FIG. 3(b), when the operator sets an imaging method (pulse sequence) and its parameters via the input means, the sequencer 104 accepts the data (step 311) and the RF controller 304 calculates an SAR value according to the condition being set (step 312). When the SAR value being calculated exceeds a predefined safety level value, the size of the flip angle in the non-imaging mode and in the imaging mode of the pulse sequence is reduced according to a predetermined modulation pattern (step 313), so that the SAR value falls into the safety level range. On this occasion, a maximum value of the flip angle is assumed as the flip angle which is set in the step 311. As a method for calculating the SAR value in the step 312, for example, an SAR value is obtained beforehand experimentally by one-time RF irradiation, and according to the number of RF irradiation times, the SAR value for overall imaging is calculated. A modulation pattern of the flip angle will be described later.

It is further possible to configure such that the step 311 and the step 312 are omitted, and the modulation pattern is defined so that the SAR is reduced at a predetermined constant rate. In this configuration, a constant may be set as the reduction rate, or the operator may set the rate as an imaging parameter. Another configuration may be possible such as monitoring the SAR value in real time by an external device, and setting the modulation pattern by a feedback control so that the SAR value does not exceed the safety level during the imaging.

When the imaging starts, the radio frequency pulse generator 106 controls amplitude of the radio frequency pulse, responding to the timing controller 301 and the RF controller 304 of the sequencer 104, and allows the RF coil 107 to generate an RF pulse at a predetermined flip angle (step 314). The RF probe 108 receives a signal generated from the subject 103 and the receiver 109 performs detection thereof. Thereafter, the computer 110 corrects the echo intensity as required, and then an image is reconstructed (step 315).

As a method of the correction, it is possible to correct the echo intensity according to the flip angle at which irradiation is performed. In addition, the signal processor is capable of correcting the echo intensity detected by the RF pulse whose flip angle is smaller than a maximum value, for example, so that it agrees with the echo intensity detected by the RF pulse whose flip angle is a maximum value.

Figure 4A:
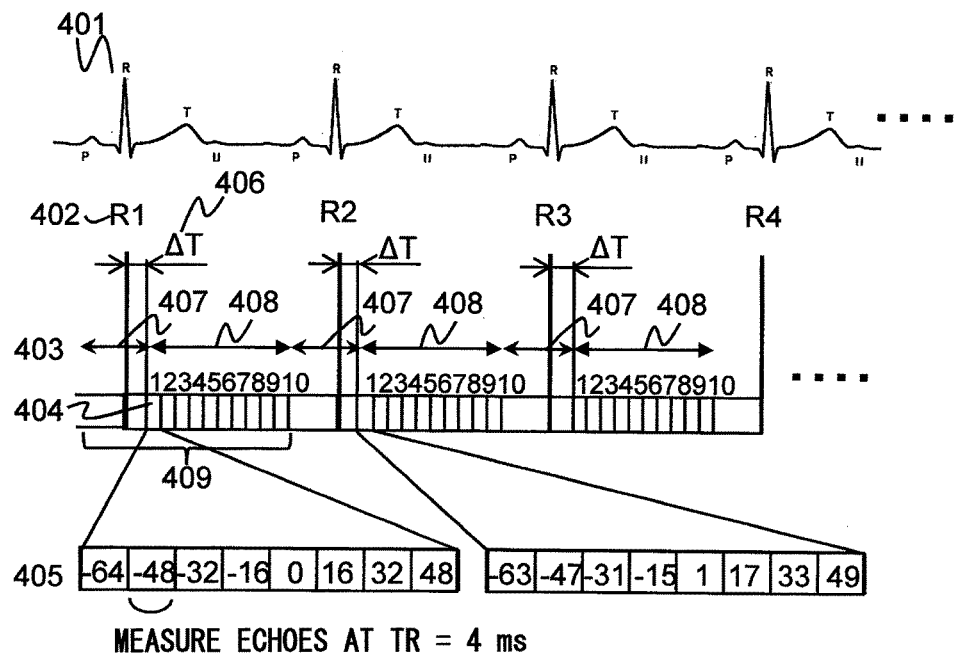
FIG. 4(a) illustrates a relationship between the ECG gating and the measurement according to the gating method of the first embodiment and FIG. 4(b) illustrates the k-space thereof.
Figure 4B:
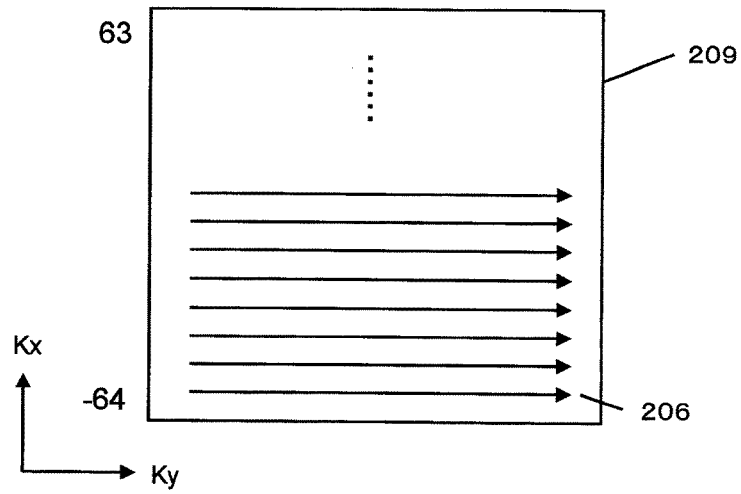

Hereinafter, an explanation will be made as to cine imaging and the flip angle control, when a gating method is used as an ECG-gated method. FIG. 4 illustrates an example of the cine imaging, showing a relationship between the electrocardiogram 401 and the measurement 403, in the case where an image of 128×128 is taken, under the condition that 10 frames for one heartbeat and TR=4 ms. Firstly, in the non-imaging mode 407, a detection of the first R wave is waited. Next, after a lapse of the delay time ΔT 406 from the clock time R1 of the R wave, the measurement is performed from the phase encoding amount −64 to 48, while changing the phase encoding amount 405 by 16 (frame 404). This measurement is repeated for 10 frames, i.e., ten times in total (imaging mode 408). Thereafter, the next detection of R wave is again waited in the non-imaging mode 407. After a lapse of the delay time ΔT from the clock time R2 of the R wave, the measurement is performed from the phase encoding amount −63 to 49, while changing the phase encoding amount by 16 in the same manner. This measurement is repeated for 10 frames, i.e., ten times in total (imaging mode 408). As shown in FIG. 4(b), after the measurement as described above is conducted successively until R16, the echoes 206 are rearranged according to the phase encoding order as to the frame 404 in the same phase, to be placed in the k-space 209, thereby performing the reconfiguration.

Next, with reference to FIG. 5, an explanation will be made as to the control of the flip angle in the cine imaging as explained above.

Here, the flip angle set by the user via the input means is assumed as a maximum flip angle αmax. In the present embodiment, the non-imaging mode preparing for detecting the R wave and the imaging mode for measuring an echo after the detection of R wave are assumed as one measurement set 409 (see FIG. 4(a)). By using this measurement set 409 as a unit, a control is performed for setting the flip angle as to each measurement set 409. Firstly, the flip angle controller 304a of the sequencer 104 discriminates in all the measurement sets 409, between the measurement set 409 for applying a phase encoding amount having a minimum absolute value (referred to as measurement set (i) 501), and the other measurement set 409 (referred to as measurement set (ii) 502).

Figure 5:
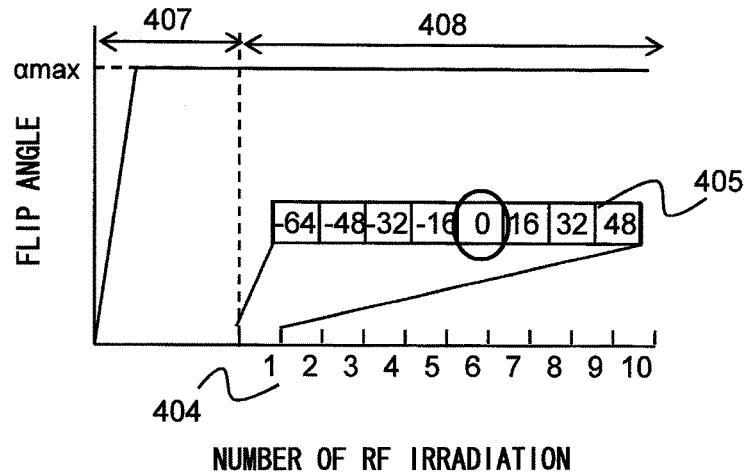
FIG. 5 illustrates an example of the measurement and the control of a flip angle according to the present embodiment.
Figure 5:
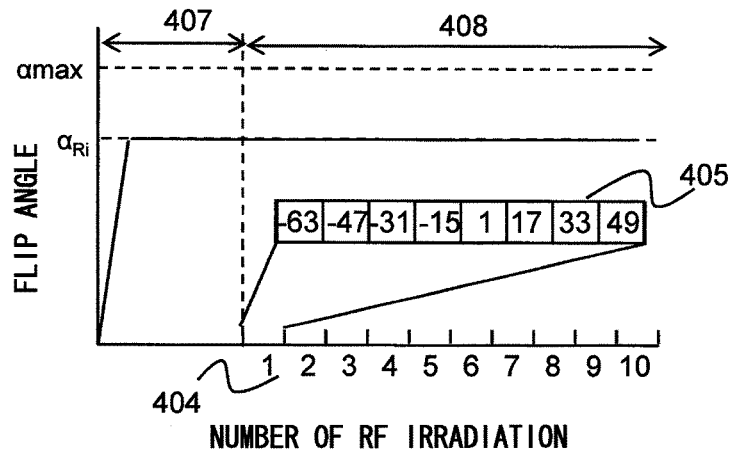

FIG. 5 illustrates on example showing the relationship between each of the measurement sets 409 and the flip angle. As for the measurement set (i) 501 for applying the phase encoding amount having the minimum absolute value, the flip angle controller 304a sets a maximum value (αmax) as the flip angle in the measurement set, substantially as constant. Here, being substantially as constant indicates that there is an error within 10%. As for the flip angle in the non-imaging mode 407, it is also possible to perform modulation which gradually increases the flip angle, so that the steady state is established in its early stages. It is preferable that the modulation of the flip angle in the non-imaging mode 407 is configured aiming that the flip angle becomes approximately the same as the maximum flip angle (αmax) in its early stages. Accordingly, it is possible to enhance an effect for maintaining the contrast of the image. The modulation may be linear or nonlinear, but preferably, it should be nearly sequential. Consequently, it is possible to reduce artifact when an image is reconstructed.

As shown in FIG. 5, as for the measurement set (ii) 502 which does not apply the phase encoding amount having the minimum absolute value, the flip angle $\alpha_{Ri}$ is set to be in the range between or equal to 0 and αmax. With this setting, reduction of SAR is performed. The flip angle being set here is assumed as the maximum flip angle $\alpha_{Ri}$ in this measurement set. In the imaging mode 408 of the measurement set (ii), it is preferable that $\alpha_{Ri}$ is substantially constant. This is because it may enhance an effect to maintain the image contrast. However, it is possible to perform modulation in the imaging mode 408, and in this case, it is preferable to repeat a similar modulation in each frame 404 within the imaging mode 408. Accordingly, variations in contrast for each frame can be suppressed when reconstructing an image. On the other hand, in the non-imaging mode 407, any modulation may be possible, but it is preferable to keep the value of the flip angle to be sequential when shifting to the imaging mode 408. Consequently, it is possible to reduce the artifact when reconstructing an image.

Figure 6A:
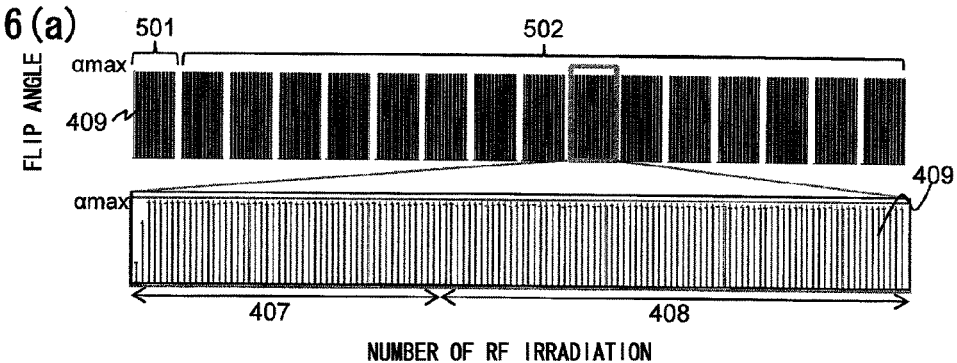
FIG. 6(a) illustrates a conventional control of the flip angle, and the figures from FIG. 6(b) to FIG. 6(d) illustrate the examples for controlling the flip angle in the present embodiment.
Figure 6B:
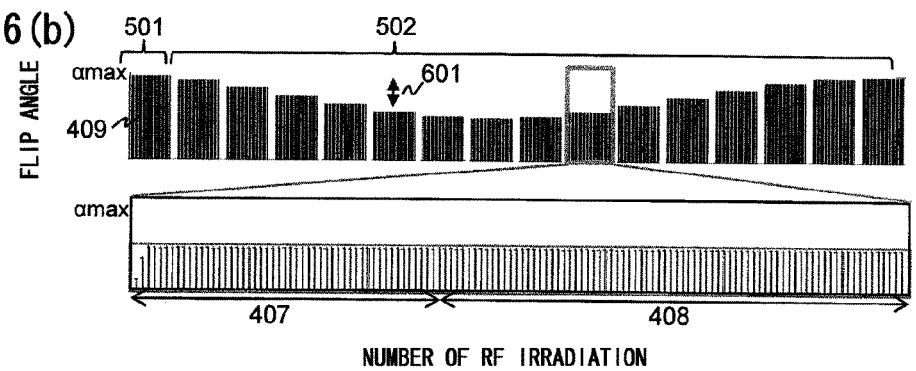
Figure 6C:
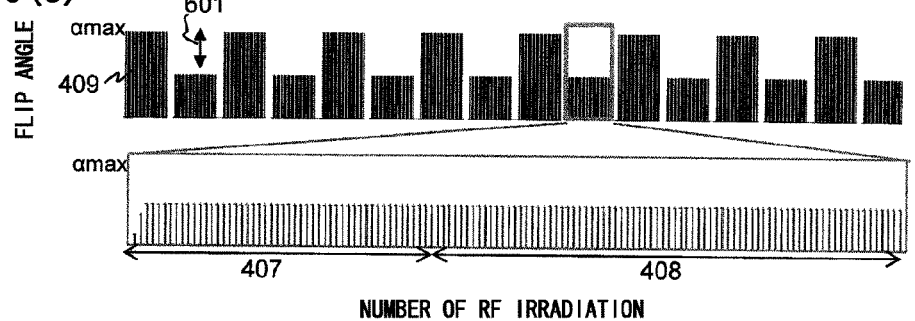
Figure 6D:
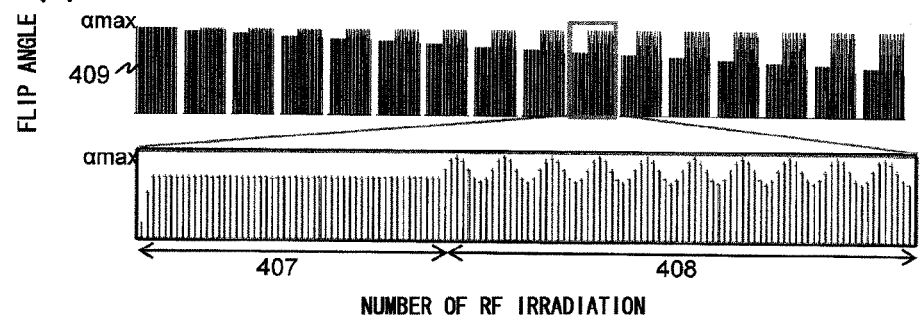

Figures from FIG. 6(b) to FIG. 6(d) illustrate examples of the flip angle modulation which are conducted by the flip angle controller 304a in the step 313 in FIG. 3(b), in the measurement sequence shown in FIG. 4 according to the present embodiment. FIG. 6(a) shows a conventional example. In each of FIG. 6(a) to FIG. 6(d), the upper stage shows the variation of the flip angle for the overall measurement, and the lower stage shows the variation of the flip angle in one partial measurement set. In each of FIG. 6(a) to FIG. 6(d), the first measurement set 409 corresponds to the measurement set (i) 501 including the phase encoding amount having a minimum absolute value, and the other measurement sets correspond to the measurement sets (ii) 402 which do not include the phase encoding amount having the minimum absolute value. The maximum flip angle αmax is 60 degrees.

In the conventional imaging method as shown in FIG. 6(a), the flip angle is kept constant in all the measurement sets 501 and 502, except the modulation at the time of rising in the non-imaging mode 407.

The sequence as shown in FIG. 6(b) to which the flip angle control of the present embodiment is applied, considers that the echo intensity depends on the flip angle, and configures such that the flip angle as to each measurement set 409 is varied smoothly in sequential manner in time series, so that the flip angle varies smoothly when the echoes being measured are arranged in the k-space 209. In other words, the flip angle controller 403a sets a maximum flip angle αmax to the first measurement set (i) 501 including a phase encoding amount having an absolute value being minimum, reduces the flip angle sequentially in time series as to each measurement set 409, so that the SAR for the overall imaging pulse sequence falls into a predetermined safety level range, and then, increases again the flip angle until the flip angle αmax which is set to the final measurement set 409. A reduced amount 601 is determined by calculation according to the predefined safety level range. The flip angle is constant during the imaging mode 408 within each of the measurement sets 409. In the non-imaging mode 407, the flip angle is small only at the rising part. It is increased immediately to be the same flip angle as that of the imaging mode 408. As the sequence shown in FIG. 6(b), by varying the flip angle as to each of the measurement sets 409 smoothly in time series, it is possible to expect an effect to suppress artifacts which may occur in the reconstructed image.

In the sequence as shown in FIG. 6(c), a large flip angle and a small flip angle are set alternately for each of the measurement sets 409. The flip angle controller 403a sets a maximum flip angle αmax to the first measurement set (i) 501 including the phase encoding amount having a minimum absolute value, and for the subsequent measurement sets (ii) 502 not including the phase encoding amount having the minimum absolute value, the flip angle is reduced one after the other by turns, thereby configuring the SAR of the overall imaging pulse sequence to fall into the predetermined safety level range. The reduced amount 601 of the measurement set 409 as to which the flip angle is reduced is determined by calculation according to the predefined safety level range. Consequently, SAR is made to fall into the safety level range within an extremely short period of time, which corresponds to the time for two measurement sets 409, and it is possible to achieve an effect that loads on the subject 103 are reduced.

The sequence as shown in FIG. 6(d) is an example that the flip angle in the imaging mode 408 is varied for each frame 404 in the measurement set (ii) 502 which does not apply the phase encoding amount having the minimum absolute value. Accordingly, when the measured echoes are arranged in the k-space, the variation of the flip angle is made smoother than that of the sequence of FIG. 6(b), and it is possible to expect an effect to suppress artifacts which may occur in the reconstructed image. It is to be noted here that in the measurement set (i) 501 which applies the phase encoding amount having the minimum absolute value, the maximum flip angle (αmax is set and it is not modulated for any frame 404. In the measurement set (ii) 502 in which the modulation is performed, it is preferable that echoes to which the maximum value flip angle is applied by the modulation are associated with echoes in a low frequency area having a relatively small absolute value of the phase encoding amount in the measurement set 409; and echoes to which the minimum value flip angle is applied are associated with the echoes in the high frequency area having a relatively large absolute value of the phase encoding amount. It is further preferable to set the same flip angle to the echoes to which the same phase encoding amount is applied within the measurement set 409. Consequently, it is possible to expect an effect that frame-by-frame fluctuations in contrast may be suppressed.

Figure 7:
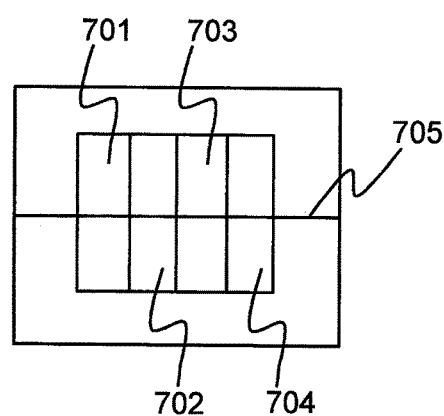
FIG. 7 illustrates a subject model which is subjected to the imaging in the present embodiment.

Next, there will be explained results of the imaging performed by the imaging sequence as shown in FIG. 6(a) and FIG. 6(b). As the pulse sequence, the phase compensation type two-dimensional GrE pulse sequence as shown in FIG. 2 was employed, and the imaging parameters were assumed as those shown in FIG. 4; TR=4 ms, TE=2 ms, matrix size=128×128, the number of frames is 10, and the number of echoes is eight, which are acquired by each frame within one heartbeat. Inhere, the R-R interval is kept constant at all times, and the number of RF irradiation times is fixed to fifty in the non-imaging mode. FIG. 7 illustrates the imaging target. The reference numerals 701 to 704 are used to indicate a combination of four types of $T_1$ and $T_2$. Here, $T_1$ and $T_2$ respectively correspond to 701: 800, 160, 702: 800, 80, 703: 400, 160, and 704: 400, 80 ms.

Figure 8A:
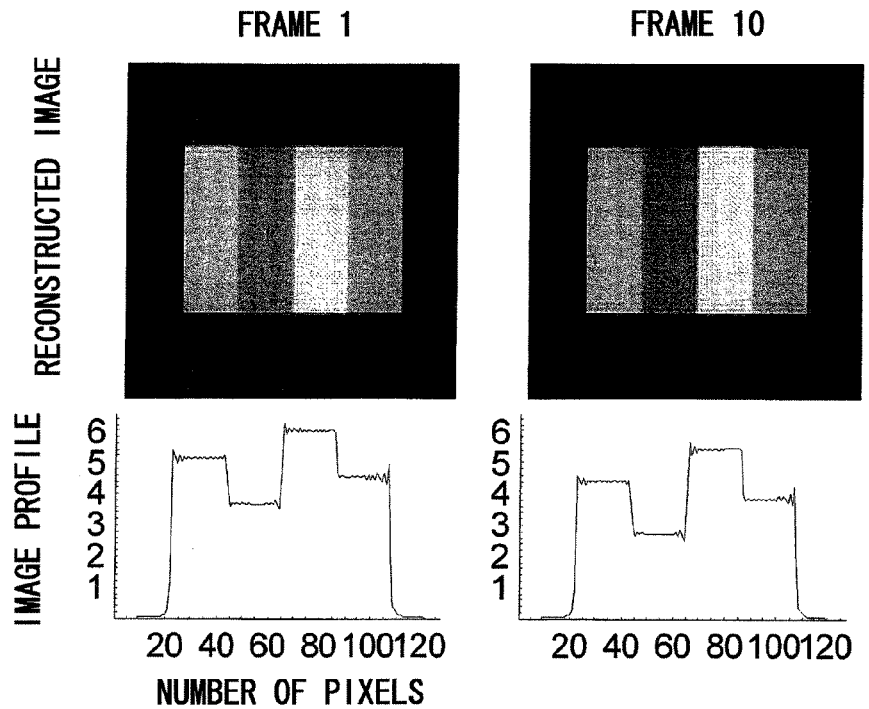
FIG. 8(a) illustrates a result of the conventional imaging.
Figure 8B:
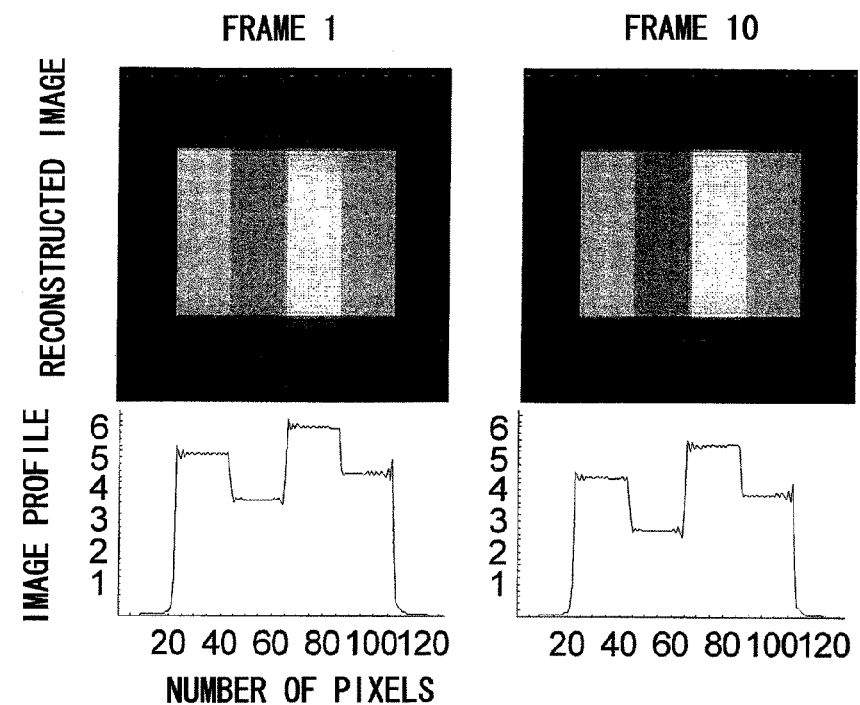
FIG. 8(b) illustrates the imaging according to one embodiment of the present invention.

FIG. 8 illustrates reconstructed images in the 1st frame and in the 10th frame, and profiles at the line 705. FIG. 8(a) shows a result of FIG. 6(a), and FIG. 8(b) shows a result of FIG. 6(b) to which the present invention is applied. When these are compared, it is found that the S/N ratio and the image contrast are approximately equivalent to each other. On the other hand, as for the SAR, it is reduced by approximately 41% in the imaging of (b), compared to the imaging of (a). According to the effect of this SAR reduction, it is possible to achieve an imaging which satisfies the safety level, while maintaining image quality in a high magnetic field device.

In order to perform the image reconstruction, the signal processor 110 carries out an operation such as Fourier transform by using the echoes which are measured in the imaging mode 408 and the image is reconstructed. On this occasion, since flip angles different as to each of the measurement sets 409 are set, there are variations of intensity in the echoes acquired by such different flip angles. The signal processor 110 is also capable of correcting the intensity of the measured echoes according to the flip angles. Consequently, it is possible to reduce blurring of the image or ghosts, generated in the reconstructed image.

When the measured echoes are arranged in the k-space, the aforementioned imaging method as shown in FIG. 4 considers allocation of the phase encoding amount 405 as to each of the measurement sets 409, so that fluctuations in the measurement time of adjacent echoes are smoothened. Another method for allocating the phase encoding amount 405 is to divide the phase encoding, in such a manner that the measurement is performed from −64 to −57 varying the phase encoding one by one, in the frame 404 of the first measurement set 409 as shown in FIG. 4; and the measurement of the phase encoding is performed from −56 to −49 in the measurement set 409 at the next R wave clock time. Accordingly, when the flip angle is controlled as shown in FIG. 6(b), it is possible to suppress the fluctuations of the flip angle of the echoes which are arranged in the k-space. As a result, there is an effect that artifacts are suppressed in the reconstructed image. It is to be noted that the measuring sequence of the measurement sets may be rearranged in any order. In the aforementioned embodiment, the measurement set including the echoes having a minimum absolute value of the phase encoding is initially measured. However, if achieving of the steady mode in magnetization is taken into account, measuring this set at the last may be preferable.

Second Embodiment

Figure 9:
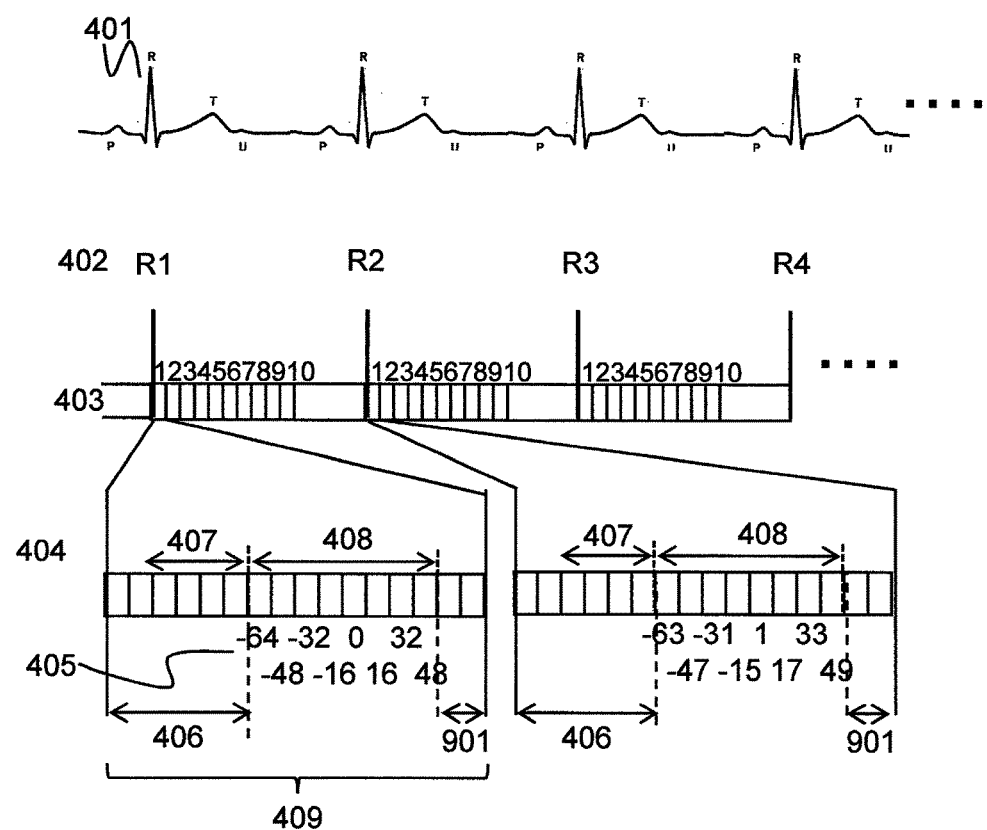
FIG. 9 illustrates a relationship between the ECG gating according to the triggering method and the measurement in the second embodiment.

As a second embodiment, an explanation will be made as to an example in which the present invention is applied to ECG-gating according to a triggering method. An imaging apparatus similar to the apparatus as shown in FIG. 1 is employed. An imaging sequence similar to the sequence as shown in FIG. 2 is employed. With reference to FIG. 9, the triggering method will be explained. Firstly, within the delay time ΔT 406 which is set starting from the time of R wave R1 402, the steady state of magnetization is obtained in the non-imaging mode 407. Then, after a lapse of the ΔT 406, the phase encoding 405 is measured from −64 to 48 with the changes by 16 (imaging mode 408). Thereafter, measurement of the next frame 404 is performed after the lapse of the time interval ΔI 901. This is repeated for 10 frames, corresponding to ten measurements in total. In the next cardiac cycle of from the R wave R2, the phase encoding is measured from −63 to 49, in the similar manner. The measurement as described above is conducted sequentially until R16. This gating method is advantageous because it enables irradiation of prepulse such as fat suppression, immediately before the non-imaging mode.

Figure 10:
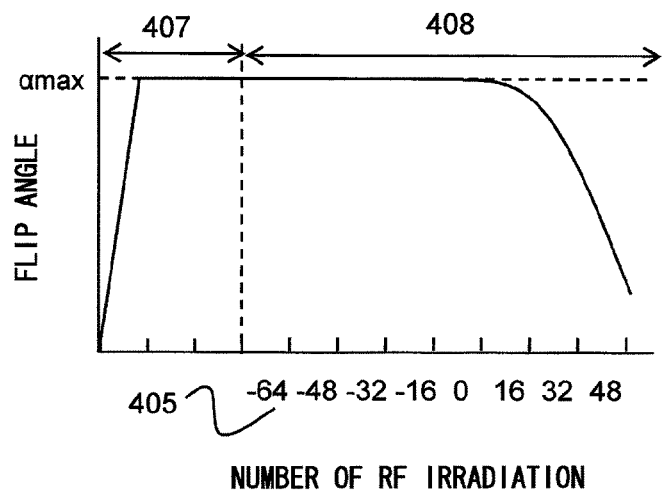
FIG. 10 illustrates an example of the measurement and the control of the flip angle in the second embodiment.

With reference to FIG. 10, a method for controlling the flip angle in the gated imaging according to the triggering method will be explained. Here, the non-imaging mode 407 and the imaging mode 408 for measuring one frame are assumed as the measurement set 409 (see FIG. 9), and the size of the flip angle is controlled in a unit of the measurement set 409. In measuring echoes, the flip angle controller 403a discriminates the measurement sets between (i) the measurement set including the measurement of echoes having a minimum absolute value of phase encoding, and the other measurement set (ii).

As for the measurement set (i) including the measurement of the echoes that has a minimum absolute value of the phase encoding, the flip angle at which the RF pulse is irradiated is set to be the maximum αmax and substantially constant, except the flip angle at the rising part of the non-imaging mode 407. The maximum flip angle αmax is maintained at least until the time point when the phase encoding having the minimum absolute value (the phase encoding amount is zero in the case of FIG. 10) is applied to measure echoes. Thereafter, it is further possible to reduce the flip angle as shown in FIG. 10.

Accordingly, the echoes acquired by applying the phase encoding having the minimum absolute value are not only generated from the RF pulse irradiated immediately before, but also from the magnetization which is sufficiently in the steady state after continuously applying the RF pulses at the maximum flip angle αmax in the non-imaging mode 407 (except the rising time) and in the imaging mode 408 until that point of time. Consequently, sufficiently strong echo signals can be acquired and it is possible to maintain the image contrast and S/N ratio.

For the case of the measurement set (ii) which does not include the phase encoding having the minimum absolute value, it is configured such that the flip angle is reduced as shown in FIG. 6(b) to FIG. 6(d) similar to the gating method of the first embodiment as explained. Accordingly, it is possible to allow the SAR to fall into the safety level range.

It is to be noted that as shown in FIG. 10, after applying the phase encoding having the minimum absolute value (phase encoding amount is zero in the case of FIG. 10), the flip angle may be decreased to be equal to or smaller than the maximum value αmax, or it is further possible to maintain the maximum value αmax. In the case where the flip angle is decreased, any modulation may be applicable, such as monotone decreasing, or a combination of monotone decreasing and monotone increasing. By the decrease from the maximum value αmax as described above, it is possible to further reduce SAR. It is to be noted that if the maximum value αmax is held without the reduction in the latter part, it is expected to enhance the effect that the image contrast is maintained.

Third Embodiment

As the third embodiment, there will be explained an example in which the present invention is applied to a retrospective ECG-gated method. An imaging apparatus similar to the apparatus as shown in FIG. 1 is employed. An imaging sequence similar to the sequence as shown in FIG. 2 is employed. In the embodiment as described above, a prospective ECG gated method has been explained, which determines in advance the number of frames, the imaging time for one frame, and the like, on the basis of an average heart rate of the subject, before starting the imaging. On the other hand, there is a retrospective ECG gated method in which an electrocardiogram is recorded in parallel with the imaging, and signals are rearranged by post processing based on the recorded information. This method has a merit that it is impervious to being influenced by the variations in heart rate.

Figure 11:
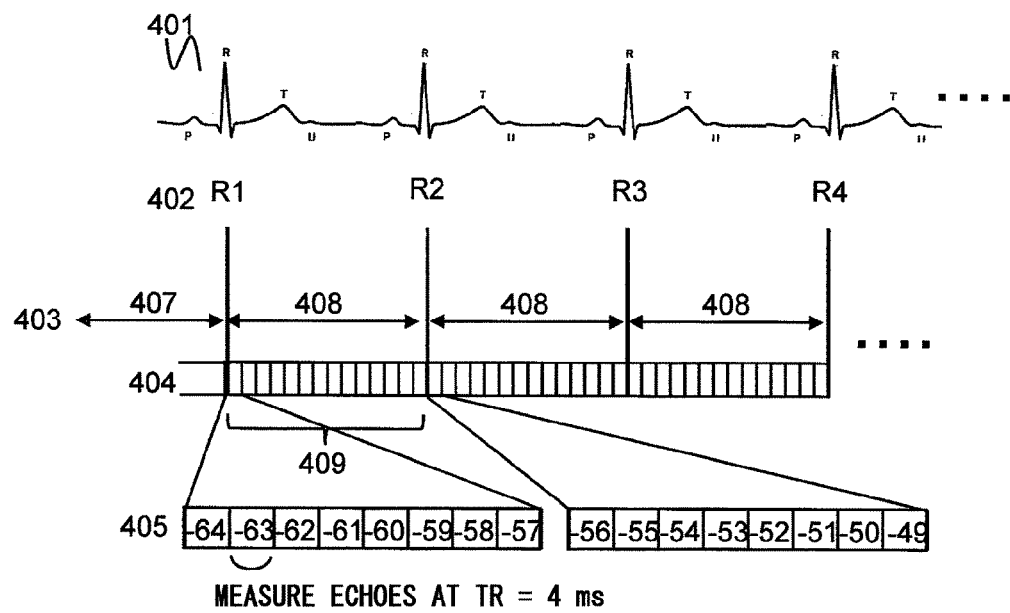
FIG. 11 illustrates a relationship between a retrospective ECG gated method and the measurement in the third embodiment.

With reference to FIG. 11, an explanation will be made as to the imaging method according to the retrospective ECG gated method. Firstly, a first detection of R wave is waited in the non-imaging mode 407. Next, the phase encoding amount 405 is measured, in the variation from −64 to −57 one by one, immediately after the clock time of R wave R1. This measurement is carried out repeatedly until the clock time when the next R wave is detected (imaging mode 408). On this occasion, the time taken for measuring the echoes is measured in the similar manner. Next, the phase encoding amount is measured in the variation from −56 to −49 one by one, immediately after the clock time of R wave R2. This measurement is carried out repeatedly until the next R wave is detected (imaging mode 408). The measurements as described above are conducted sequentially until R16. Thereafter, in each time phase, the echoes required for reconstructing an image are collected, based on the time taken for measuring the echoes required for the image reconstruction.

Figure 12:
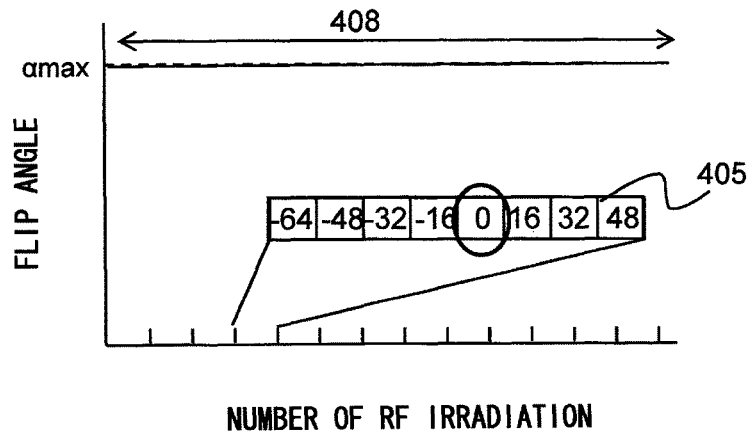
FIG. 12 illustrates an example of the measurement and the control of the flip angle in the third embodiment.
Figure 12:
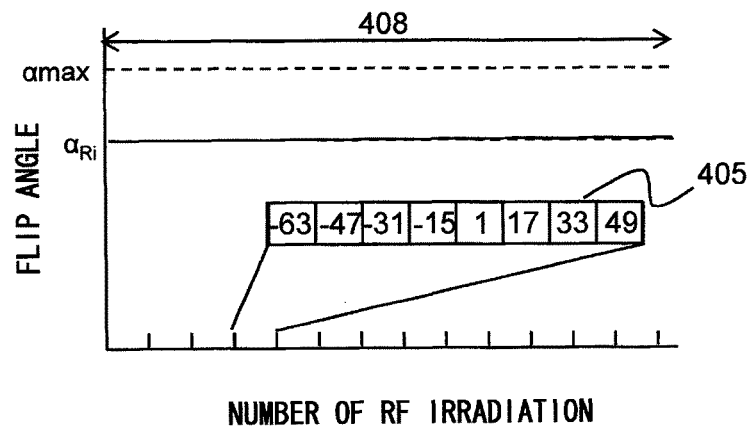

With reference to FIG. 12, an explanation will be made regarding the flip angle control in the retrospective ECG gated method according to the present invention. In here, the flip angle is controlled assuming the imaging mode 408 for every R wave clock time as the measurement set 409 (see FIG. 11). The flip angle controller 304 discriminates the measurement sets between the measurement set (i) 501 including the measurement of echoes with the phase encoding having a minimum absolute value in the echo measurement, and the other measurement set (ii) 502. FIG. 12 shows the examples of the flip angle in the measurement set (i) and in the measurement set (ii). The flip angle in the measurement set (i) 501 is assumed as maximum αmax, and it is controlled to be substantially constant. Accordingly, the image contrast and the S/N ratio are maintained.

Furthermore, it is preferable that the flip angle of the RF pulses in the measurement set 409 measured one set before the measurement set 501 or in the non-imaging mode 407 is also set to the maximum αmax and substantially constant. Accordingly, this may enhance the effect that the image contrast is maintained. The flip angle in the measurement set (ii) is made lower than the maximum value αmax. Any method may be employed for reducing the flip angle, but it is preferable that it varies in almost sequential manner with the flip angle of the measurement set 409 measured before and that of the measurement set 409 measured after. Accordingly, it is possible to suppress the occurrence of artifacts when an image is reconstructed.

It is to be noted that in the aforementioned embodiment, an explanation has been made as to the cine imaging of the heart, but the portion targeted for imaging is not limited to the heart. An electrocardiogram is employed as a method for monitoring the cardiac cycle, but alternatively, other signals relating to the cardiac cycle may be applicable, such as a pulse wave.

Fourth Embodiment

The present embodiment is premised on that imaging of multiple time phases is performed. However, it is also applicable to one specific time-phase imaging. As the fourth embodiment, an example will be explained in which the present invention is applied to a single-phase synchronous imaging. An imaging apparatus similar to the apparatus as shown in FIG. 1 is employed. An imaging sequence similar to the sequence as shown in FIG. 2 is employed. Delayed contrast radiography, dynamic MRI, and the like, may be taken as application examples. Typically, the delayed contrast imaging is a method of imaging T1 weighted image after a lapse of approximately 15 minutes from dosage of contrast medium, and extracts a myocardial infarct area or a fibrotic area, as high intensity signals. In this method, the imaging is carried out with addition of IR (Inversion Recovery) pulses, so as to acquire intensive image contrast between a normal myocardium and an abnormal myocardium. On this occasion, test scanning is necessary to figure out a temporal change of TI (Inversion Time) of the normal myocardium. Multiphase imaging is performed only for the test scanning. Dynamic MRI is a method for observing a temporal change of tissue after a dosage of MRI contrast agent. An example of diagnostic method using this is myocardial perfusion. In general, the myocardial perfusion observes the dynamic state of the first path of myocardium after bolus administration of MRI contrast agent, thereby evaluating an ischemic area. Since it is necessary to use fat suppression in parallel, saturation pulses are added. Furthermore, the imaging is performed at multi-slice.

Figure 13:
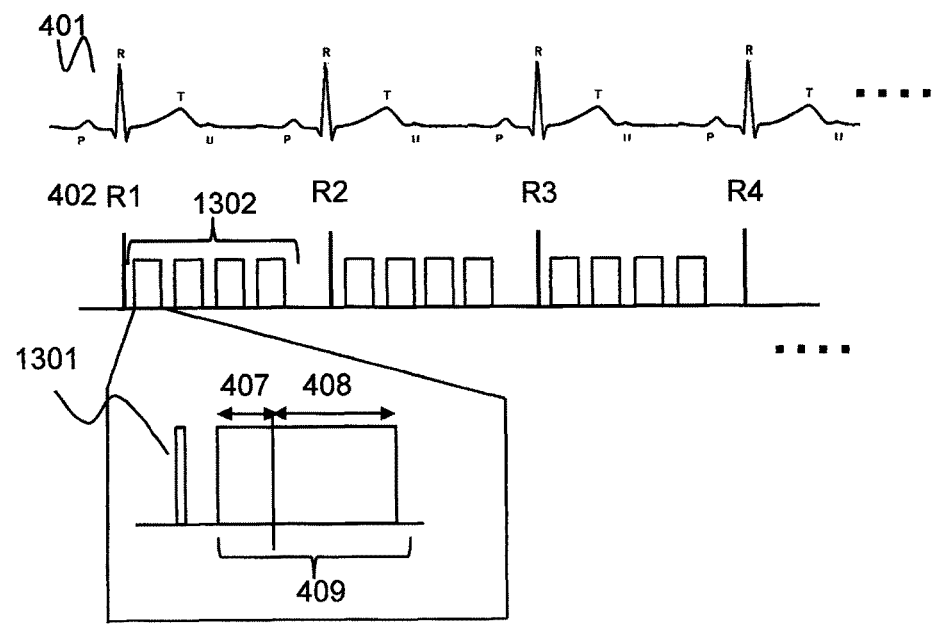
FIG. 13 illustrates a relationship between a single-phase ECG gated method and the measurement in the fourth embodiment.

In the imaging methods as described above, a prepulse is required, and therefore the triggering method is used as a gating method. FIG. 13 shows a relationship between the ECG-gating and the measurement. In the cardiac cycle shown in FIG. 13, when the delay contrast imaging is performed, imaging is carried out for multiple times as to the slice on the same position. In the case of myocardial perfusion, imaging of different slices is performed (sequence group 1302). In each of the measurements, the prepulse 1301 such as IR pulse or fat suppression is added. In the present embodiment, the non-imaging mode and the imaging mode after the prepulse are assumed as the measurement set 409 (see FIG. 13), and the flip angle is controlled. The control method is the same as the control according to the triggering method which has been explained in the aforementioned embodiment (see FIG. 5).

The embodiment described above is applicable to MRA (MR angiography) which performs imaging only in a certain time phase for arteriovenous separation.

Further in the embodiment described above, imaging of a portion which is influenced by body motion due to respiration is typically performed while holding breath. The present invention is also applicable to the case where the respiratory gated method is used under the condition of free respiration.

Fifth Embodiment

Figure 14:
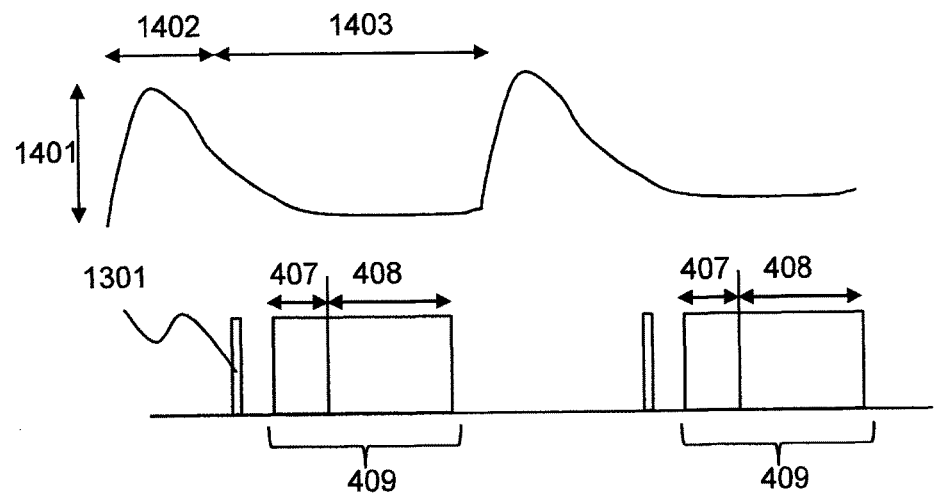
FIG. 14 illustrates a relationship between the respiratory gated method and the measurement in the fifth embodiment.

In the imaging of the abdominal region, synchronization with a cardiac cycle or pulsating is not necessarily required. However, in the imaging which takes long time, it is not possible to perform the imaging all at once under the condition of breath hold, and therefore the respiration gating is necessary. As the fifth embodiment, there is shown an example in which the present invention is applied to the imaging with the respiration gating under free respiration. An imaging apparatus similar to the apparatus as shown in FIG. 1 is employed. An imaging sequence similar to the sequence as shown in FIG. 2 is employed. For example, 3D MRCPA (MR Cholangiopancreato Angiography) is one of the applications, which is used for diagnosis of disease of biliary system and pancreas. FIG. 14 illustrates a relationship between the body motion due to respiration and the measurement. In the respiration gated method under free respiration, a respiration monitor monitors abdominal movement 1401. A respiration cycle includes inspiration 1402 and expiration 1403. The imaging is performed during the time of the expired air, which is less subjected to morphologic change due to a depth of respiration. In some cases, fat suppression is used in parallel with the MRCPA, and the imaging according to the triggering method is typically performed. As for the control of the flip angle, the non-imaging mode and the imaging mode within one respiration cycle are assumed as the measurement set 409 (see FIG. 14), and the control is performed. A method for the control is the same as the control of cine imaging according to the triggering method.

The imaging using the respiration gated method is applicable to the cine imaging in a respiration cycle. This is effective for the imaging to perform observation of diaphragm motion.

Sixth Embodiment

In the embodiment described above, an explanation has been made as the case where a synchronous imaging is required. As the sixth embodiment, an example will be explained in which the present invention is applied to an asynchronous multi-slice imaging. An imaging apparatus similar to the apparatus as shown in FIG. 1 is employed. An imaging sequence similar to the sequence as shown in FIG. 2 is employed. For example, 2D MRCPA, MRA, and the like, are included as its applications. In the asynchronous multi-slice imaging, one slice is assumed as the measurement set. In the case of multi-slice, all the measurement sets include measurement of echoes with the phase encoding amount having a minimum absolute value. Therefore, all of the measurement sets correspond to the measurement set (i) described in each of the embodiments described above. In the present embodiment, a maximum flip angle $\alpha_{max}$ is set for a predetermined period of time before the point of measuring the echo to which the minimum phase encoding amount is applied. Accordingly, it is possible to reduce SAR without reducing the intensity of echo to which the minimum phase encoding amount is applied.

Figure 15A:
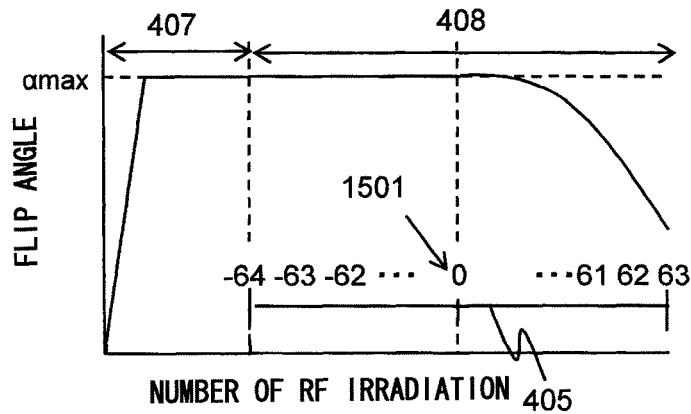
FIG. 15(a), FIG. 15(b), and FIG. 15(c) illustrate examples of the measurement and the control of the flip angle in the sixth embodiment.
Figure 15B:
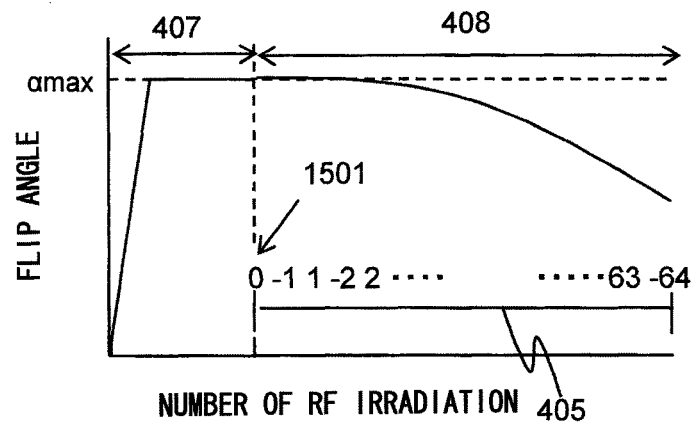
Figure 15C:
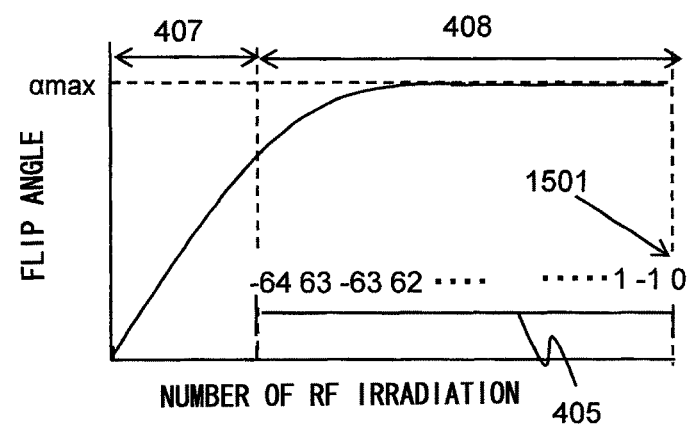

Figures from FIG. 15 (a) to FIG. 15 (c) show control examples to reduce the flip angle according to the order of the phase encoding measurement. FIG. 15(a), FIG. 15(b), and FIG. 15(c) respectively show the case where the phase encoding is measured from −64 to 63, varied one by one, the case where the measurement is performed from 0, −1, and 1, in ascending order of the absolute values of the phase encoding amount, and the case where the measurement is performed from −64, 63, and −63, in descending order of the phase encoding amount. It is to be noted that the above examples indicate the order for measuring the phase encoding that is generally used, and the order for adding the phase encoding is not limited to those examples.

In any of the figures FIG. 15(a) to (c), the flip angle is controlled so that the flip angle of the RF pulse 1501 is set to be the maximum αmax, i.e., the RF pulse for measuring the echo having the minimum absolute value of the phase encoding amount and a predetermined number of RF pulse, at least one, irradiated before that pulse 1501; and the flip angle of the RF pulse other than those pulses is set to be a value smaller than the maximum. This relates only to the irradiation order of the RF pulse for measuring the echo having the minimum absolute value of the phase encoding amount and the other RF pulse, irrespective of the imaging mode 408, the non-imaging mode 407, or the amount of the phase encoding. As for the RF pulses irradiated before the pulse with the phase encoding amount having the minimum absolute value, it is preferable to continuously maximize the flip angle of the RF pulses as many as possible. Accordingly, it is possible to acquire echoes from the magnetization which sufficiently becomes the steady state similar to the case where the measurement is performed with a constant flip angle, and SAR can be reduced while maintaining the S/N ratio and the image contrast.

In the figures from FIG. 15(a) to FIG. 15(c), it is preferable that the variation of the flip angle is sequential. This is effective for suppressing the occurrence of image artifacts. As for the flip angle which is set to be equal to or smaller than the maximum αmax, it is preferable to configure such that there is a smooth change between the first flip angle and the last flip angle in the imaging mode 408. This is because this configuration is effective for suppressing the occurrence of image artifacts, in the case where imaging of the same portion is continuously repeated, such as fluoroscopic imaging.

Explanations have been made as to the case that a phase compensation type GrE pulse sequence having a more strict SAR condition is employed as the imaging method, in the embodiment in which the flip angle is controlled. Here, it is to be noted that the control of the flip angle is not limited to using the phase compensation type GrE pulse sequence, and it is commonly used to any GrE-type pulse sequence.

DENOTATION OF REFERENCE NUMERALS

101 . . . MAGNET FOR GENERATING A STATIC MAGNETIC FIELD, 102 . . . GRADIENT MAGNETIC FIELD COIL, 103 . . . SUBJECT, 104 . . . SEQUENCER, 105 . . . GRADIENT MAGNETIC FIELD POWER SUPPLY, 106 . . . RADIO FREQUENCY PULSE GENERATOR, 107 . . . RF PROBE, 108 . . . RF PROBE, 109 . . . RECEIVER, 110 . . . SIGNAL PROCESSOR, 111 . . . DISPLAY, 112 . . . STORAGE MEDIUM, 113 . . . SHIM COIL, 114 . . . SHIM POWER SUPPLY, 115 . . . BED, 201 . . . SLICE GRADIENT MAGNETIC FIELD PULSE, 202 . . . RADIO FREQUENCY PULSE FOR MAGNETIZING EXCITATION, 203 . . . PHASE ENCODING GRADIENT MAGNETIC FIELD PULSE, 204, 205, 207 . . . READOUT GRADIENT MAGNETIC FIELD PULSE, 206 . . . ECHO, 209 . . . K-SPACE, 401 . . . ELECTROCARDIOGRAM, 402 . . . TIME OF R-WAVE, 403 . . . MEASUREMENT MODE, 404 . . . FRAME, 405 . . . PHASE ENCODING AMOUNT, 406 . . . DELAY TIME, 407 . . . NON-IMAGING MODE, 408 . . . IMAGING MODE, 501 . . . MEASUREMENT INCLUDING AN ECHO WITH A PHASE ENCODING HAVING A MINIMUM ABSOLUTE VALUE, 502 . . . MEASUREMENT NOT INCLUDING AN ECHO WITH A PHASE ENCODING HAVING A MINIMUM ABSOLUTE VALUE, 701, 702, 703, 704 . . . SUBJECT, 705 . . . POSITION WHERE AN IMAGE PROFILE IS MEASURED, 901 . . . TIME INTERVAL, 1301 . . . PREPULSE, 1302 . . . THE SAME SLICE OR A DIFFERENT SLICE, 1401 . . . ABDOMINAL MOTION, 1402 . . . INSPIRATION, 1403 . . . EXPIRATION, 1501 . . . . MINIMUM VALUE OF PHASE ENCODING ABSOLUTE VALUE

What is claimed is:

1. A nuclear magnetic resonance imaging apparatus comprising,
   a static magnetic field a application part for applying a static magnetic field to a subject,
   a gradient magnetic field application part for applying a gradient magnetic field to the subject,
   a radio frequency pulse irradiator for irradiating the subject with a radio frequency pulse,
   a detector for detecting a nuclear magnetic resonance signal from the subject, and
   a controller for controlling the radio frequency pulse irradiator, the gradient magnetic field application part, and the detector, to execute an imaging pulse sequence being predetermined, wherein,
   the controller executes one or more sequence groups, as the imaging pulse sequence, including irradiation of multiple radio frequency pulses and application of multiple gradient magnetic fields for providing multiple types of phase encoding amount, and sets a flip angle to the radio frequency pulse as to each of the one or more sequence groups,
   two or more sequence groups are provided, and the controller sets a maximum value flip angle to the sequence group which executes the phase encoding of an amount having a minimum absolute value, among the two or more sequence groups, and sets a value smaller than the maximum value as the flip angle to the other sequence group,
   the controller calculates a specific absorption rate of the imaging pulse sequence as a whole, and determines a value of the flip angle to be set to the other sequence group so that the specific absorption rate being obtained becomes equal to or less than a predetermined safety level value.

2. The nuclear magnetic resonance imaging apparatus according to claim 1, wherein,
   the sequence group comprises; a non-imaging mode which includes irradiation of the radio frequency pulse, not accompanied by a detection of the nuclear magnetic resonance signal, and an imaging mode which includes irradiation of the radio frequency pulse, accompanied by the detection of the nuclear magnetic resonance signal.

3. The nuclear magnetic resonance imaging apparatus according to claim 1, wherein,
   the controller sets a substantially constant value as the flip angle to the radio frequency pulses more than one, as to each of the sequence groups.

4. The nuclear magnetic resonance imaging apparatus according to claim 3, wherein,
   the controller executes alternately in time series, the sequence group to which the flip angle being the maximum value is set and the sequence group to which a value smaller than the maximum value is set.

5. The nuclear magnetic resonance imaging apparatus according to claim 3, wherein,
   the controller changes the flip angle sequentially in units of sequence group, for two or more sequence groups which are executed in time series.

6. The nuclear magnetic resonance imaging apparatus according to claim 3, wherein,
   the flip angle set by the controller, being substantially constant, has an error within 10%.

7. The nuclear magnetic resonance imaging apparatus according to claim 1, wherein,
the sequence group includes measurement of multiple time phases.

8. The nuclear magnetic resonance imaging apparatus according to claim 7, wherein,
in the other sequence group in which the flip angle is set to be a value smaller than the maximum value, the controller sets the same size flip angle to the radio frequency pulse to which the same size phase encoding is applied for exciting the nuclear magnetic resonance signal.

9. The nuclear magnetic resonance imaging apparatus according to claim 1, wherein,
the controller configures a value of the flip angle to be set to the other sequence group, in such a manner that the flip angle of the radio frequency pulse varies sequentially, the pulse being irradiated for detecting the nuclear magnetic resonance signal, in the case where the nuclear magnetic resonance signals being measured are arranged in accordance with the size of the phase encoding.

10. The nuclear magnetic resonance imaging apparatus according to claim 1, further comprising an image reconstruction part for reconstructing an image from the nuclear magnetic resonance signal, wherein,
the image reconstruction part corrects intensity of the nuclear magnetic resonance signal detected by the radio frequency pulse having a flip angle smaller than the maximum value, according to the flip angle at which the irradiation is performed.

11. The nuclear magnetic resonance imaging apparatus according to claim 1, further comprising an image reconstruction part for reconstructing an image from nuclear magnetic resonance signal, wherein,
the image reconstruction part corrects intensity of the nuclear magnetic resonance signal detected by the radio frequency pulse having the flip angle smaller than the maximum value, to agree with the intensity of the nuclear magnetic resonance signal detected by the radio frequency pulse having the flip angle which is the maximum value.

12. The nuclear magnetic resonance imaging apparatus according to claim 1, wherein,
the sequence group is divided into two or more, according to a cycle of body motion of the subject.

13. A nuclear magnetic resonance imaging apparatus comprising,
a static magnetic field application part for applying a static magnetic field to a subject,
a gradient magnetic field application part for applying a gradient magnetic field to the subject,
a radio frequency pulse irradiator for irradiating the subject with a radio frequency pulse,
a detector for detecting a nuclear magnetic resonance signal from the subject, and
a controller for controlling the radio frequency pulse irradiator, the gradient magnetic field application part, and the detector, to execute an imaging pulse sequence being predetermined, wherein,
the controller executes one or more sequence groups, as the imaging pulse sequence, including irradiation of multiple radio frequency pulses and application of multiple gradient magnetic fields for providing multiple types of phase encoding amount, and sets a flip angle to the radio frequency pulse as to each of the one or more sequence groups,
two or more sequence groups are provided, and the controller sets a maximum value as the flip angle to the sequence group which executes the phase encoding of an amount having a minimum absolute value, among the two or more sequence groups, and sets a value smaller than the maximum value as the flip angle to the other sequence group,
the controller sets a maximum flip angle to the radio frequency pulse within a repetition time for performing the phase encoding having a minimum absolute value and to at least one radio frequency pulse immediately before, among the radio frequency pulses more than one included in the sequence group having the minimum absolute value of the phase encoding amount, whereas the flip angle having a value smaller than the maximum value is set to the other radio frequency pulse.

14. The nuclear magnetic resonance imaging apparatus according to claim 13, wherein,
when the phase encoding in the sequence group including the phase encoding of the amount having a minimum absolute value is changed in time series from a negative minimum value to a positive maximum value, the controller sets a maximum value to an associated flip angle while the phase encoding is changed from the negative minimum value to a minimum absolute value, whereas the controller decreases the associated flip angle gradually, while the phase encoding is changed from the minimum absolute value to the positive maximum value.

15. The nuclear magnetic resonance imaging apparatus according to claim 13, wherein,
when the phase encoding in the sequence group including the phase encoding of the amount having a minimum absolute value is changed in time series from the minimum absolute value to a maximum absolute value, the controller sets a maximum value to the flip angle associated with the phase encoding having the minimum absolute value, and in the subsequent stage, the controller decreases the flip angle gradually.

16. The nuclear magnetic resonance imaging apparatus according to claim 13, wherein,
when the phase encoding in the sequence group including the phase encoding of the amount having a minimum absolute value is changed in time series from a maximum absolute value to the minimum absolute value, the controller gradually increases the flip angle in time series from when the phase encoding is the maximum absolute value, and sets a maximum value to the flip angle associated with the phase encoding having the minimum absolute value and to the flip angle associated with predetermined number of phase encoding before the phase encoding having the minimum absolute value.

* * * * *